(12) United States Patent
Kismarton et al.

(10) Patent No.: US 10,317,322 B2
(45) Date of Patent: Jun. 11, 2019

(54) COMBINED LOADING IN COMPOSITE MATERIALS

(71) Applicant: THE BOEING COMPANY, Chicago, IL (US)

(72) Inventors: Max U. Kismarton, Renton, WA (US); Samuel Eric Cregger, Kent, WA (US)

(73) Assignee: THE BOEING COMPANY, Chicago, IL (US)

(*) Notice: Subject to any disclaimer, the term of this patent is extended or adjusted under 35 U.S.C. 154(b) by 673 days.

(21) Appl. No.: 14/547,844

(22) Filed: Nov. 19, 2014

(65) Prior Publication Data
US 2016/0139016 A1    May 19, 2016

(51) Int. Cl.
*G01N 3/08*    (2006.01)
*G01N 3/24*    (2006.01)
*G06F 17/50*    (2006.01)

(52) U.S. Cl.
CPC ............ *G01N 3/08* (2013.01); *G06F 17/50* (2013.01); *G06F 17/5095* (2013.01); *G01N 3/24* (2013.01); *G01N 2203/006* (2013.01); *G01N 2203/027* (2013.01); *G01N 2203/0298* (2013.01)

(58) Field of Classification Search
CPC ...... G01N 3/08; G01N 3/24; G01N 2203/006; G01N 2203/027; G01N 2203/0298; G06F 17/50; G06F 17/5095
USPC .............................................. 703/1
See application file for complete search history.

(56) References Cited

U.S. PATENT DOCUMENTS

| | | | | |
|---|---|---|---|---|
| 7,203,628 B1* | 4/2007 | St. Ville | ............ | G06F 17/5018 264/219 |
| 8,257,826 B1* | 9/2012 | Zinn | ............ | B64G 1/58 428/310.5 |
| 8,380,776 B2* | 2/2013 | Suzuki | ............ | C08G 59/4021 702/22 |
| 9,020,786 B2* | 4/2015 | Rassaian | ............ | G01N 3/32 702/182 |
| 2003/0037620 A1* | 2/2003 | Mansky | ............ | G01N 3/02 73/862.046 |
| 2003/0054740 A1* | 3/2003 | Mansky | ............ | G01N 3/02 451/57 |
| 2007/0100565 A1* | 5/2007 | Gosse | ............ | G06F 17/5018 702/34 |
| 2011/0000307 A1* | 1/2011 | Jevons | ............ | G01N 3/08 73/818 |

(Continued)

FOREIGN PATENT DOCUMENTS

JP    2008-026086 A    2/2008

OTHER PUBLICATIONS

Arnold et. al., Failure Envelopes for Notched CSM Laminates Under Biaxial Loading, 1995 Elsevier Science Limited, Composites 26 (1995) 739-747.*

(Continued)

*Primary Examiner* — Rehana Perveen
*Assistant Examiner* — Justin C Mikowski
(74) *Attorney, Agent, or Firm* — Marshall, Gerstein & Borun LLP

(57) ABSTRACT

A method for determining material failure that includes the steps of: fabricating a coupon made of a material; applying first force and second forces on the coupon, where the second force is different than the first force; and characterizing a material failure due to the application of the first force and the second force to the coupon.

14 Claims, 3 Drawing Sheets

(56) References Cited

U.S. PATENT DOCUMENTS

| | | | | |
|---|---|---|---|---|
| 2012/0287248 | A1* | 11/2012 | Erdman, III | G01N 3/068 348/47 |
| 2015/0030389 | A1* | 1/2015 | Pollett | B29C 70/545 403/404 |
| 2015/0170022 | A1* | 6/2015 | Malik | G01N 3/30 706/21 |
| 2015/0362415 | A1 | 12/2015 | Sanui et al. | |
| 2016/0103939 | A1* | 4/2016 | Kumar | G06F 17/5018 703/1 |
| 2017/0016861 | A1* | 1/2017 | Tat | G01N 29/11 |

OTHER PUBLICATIONS

Vlot et. al., Fibre Metal Laminates an Introduction, Springer Science+ Business Media, B.V., 2001, 477-497.*

Tay et. al., Damage progression by the element-failure method (EFM) and strain invariant failure theory (SIFT) Composites Science and Technology 65 (2005) 935-944.*

Tay et. al., Element-Failure: An Alternative to Material Property Degradation Method for Progressive Damage in Composite Structures, Journal of Composite Materials, vol. 39, No. 18/2005, 1659-1675.*

Afaghi-Khatibi et. al., Characterisation of fibre/matrix interfacial degradation under cyclic fatigue loading using dynamic mechanical analysis, Composites: Part A 33 (2002) 1585-1592.*

Afaghi-Khatibi et. al., An experimental study of the influence of fibre-matrix interface on fatigue tensile strength of notched composite laminates, Composites: Part B 32 (2001) 371-377.*

S.T. Pinho et. al., Fracture toughness of the tensile and compressive fibre failure modes in laminate composites, Elsevier Science, Dec. 15, 2005, pp. 1-27 (Year: 2005).*

C.E. Harris, et. al., Fracture Behavior of Thick, Laminated Graphite/ Epoxy Composites, NASA Contractor Report 3784, Mar. 1984, pp. 1-189. (Year: 1984).*

Extended European Search Report for Application No. EP15188380.8 dated Jul. 14, 2016.

Partial European Search Report for EP Application No. 15188380 dated Apr. 1, 2016.

Laffan et al., "Translaminar Fracture Toughness Testing of Composites: A Review", pp. 481-489 (2012).

Afaghi-Khatibi et al., "Characterisation of Fibre/Matrix Interfacial Degradation Under Cyclic Fatigue Loading Using Dynamic Mechanical Analysis", pp. 1585-1592 (2002).

Arnold et al., "Failure Envelopes for Notched CSM Laminates Under Biaxial Loading", pp. 739-747 (1995).

Extended European Search Report for Application No. EP15188380.8 dated Jul. 4, 2016.

European Examination Report for EP Application No. 15188380.8 dated Feb. 14, 2018.

Notice of Reasons for Rejection for JP Application No. 2015-219040 dated Mar. 5, 2019.

* cited by examiner

COMBINED LOADING IN COMPOSITE MATERIALS

FIELD

This invention relates to material testing and panel design and, more specifically, to testing and analysis of composite materials for use in panel design by applying combined forces simultaneously.

BACKGROUND

Composite panels, such as 5 stringer panels that can be used in aircraft and other products, are tested during the research and development phase of a project and must be tested during a certification process before they can be used in an aircraft or similar product. Currently, these 5 stringer panels are tested using one of three common methods. Testing of full 5 stringer panels, modeling and analyzing 5 stringer panels using computer simulation, or testing smaller sample panels (coupons) using a single tension or compression load and extrapolating the results back to a full 5 stringer panel. However, each of these current methods has its own drawbacks and inefficiencies.

For example, it can cost millions of dollars a year to manufacture and test full composite 5 stringer panels. While testing of at least one 5 stringer panel is necessary for certifying a composite structure prior to the structural design being used on an aircraft, each full 5 stringer panel can cost up to $1,200,000 and can take up to 6 months to fabricate and test. In addition, multiple 5 stringer panel tests need to be performed on new composite technologies in order to obtain a statistically meaningful data set across the range of thicknesses and layups being considered for use. Because of the long lead time and high cost, testing multiple possible designs and/or materials for a 5 stringer panel can be cost and time prohibitive and can possibly lead designers to settle for a panel design that is good enough for a particular design application instead of a panel design that is the best or optimized for a particular design application.

In addition, using computer modeling of 5 stringer panels currently does not provide the accuracy required in the research and development phase of projects. For example, current computer models cannot reliably predict failure load, failure mode, and damage trajectory. The current reliability of computer models is approximately 70-80%. That means that 20-30% of the time, this analysis methods fail to predict the results. This can result in design changes that affect program costs and schedule by pushing back final design and loads 6-12 months and spending more money to manufacture additional 5 stringer panels for testing every time this happens.

Finally, testing coupons (i.e., small sections of a material to be used in a 5 stringer panel) has been utilized in an attempt to reduce overall costs associated with new composite materials. Unfortunately, the existing coupon test method loads the coupon in a uni-axial fashion and doesn't load the material in a way that is representative of the 5 stringer panel conditions. Because of this, current coupon test methods fail to predict the performance of the 5-stringer composite panel reliably and accurately.

Therefore, there is a need for a material test method and panel design method that is low cost, fast, accurate, and reliable.

SUMMARY

In one embodiment of the present invention, a method for determining material failure is provided that comprises the steps of: fabricating a coupon made of a material; applying first force and second forces on the coupon, wherein the second force is different than the first force; and characterizing a material failure due to the application of the first force and the second force.

In another embodiment of the present invention, a method for designing a composite panel is provided that comprises the steps of: modeling the panel having a first notch and determining a combined stress state near the first notch; modeling coupon stress states to replicate the combined stress state of the panel; fabricating a plurality of coupons, each having a second notch, and testing the plurality of coupons to obtain a plurality of test results; building a database based on the test results; fabricating the panel based on the plurality of test results in the database; and testing the panel.

The features, functions, and advantages that have been discussed can be achieved independently in various embodiments or may be combined in yet other embodiments further details of which can be seen with reference to the following description and drawings.

DESCRIPTION

One method described herein provides a low cost, fast material test that can be used to more accurately and reliably determine the strength of a material, such as a composite laminate, by applying combined shear and tension/compression stresses simultaneously. Since the local loading mimics the complex loading environment of the 5-stringer panel structure, this allows for the prediction of the multi-stringer structure. This material test method can be much faster and less expensive than manufacturing and testing a full 5 stringer panel. For example, the cost of fabrication and testing one coupon using this test method could be approximately $3,000 and $5,000 per coupon, compared to the $700,000 to $1,200,000 to manufacture and test a full 5 stringer panel. This test method can also provide results that are more accurate than pure computer modeling and provide more reliable results than the current uni-axial, single force coupon testing.

Figure 1:
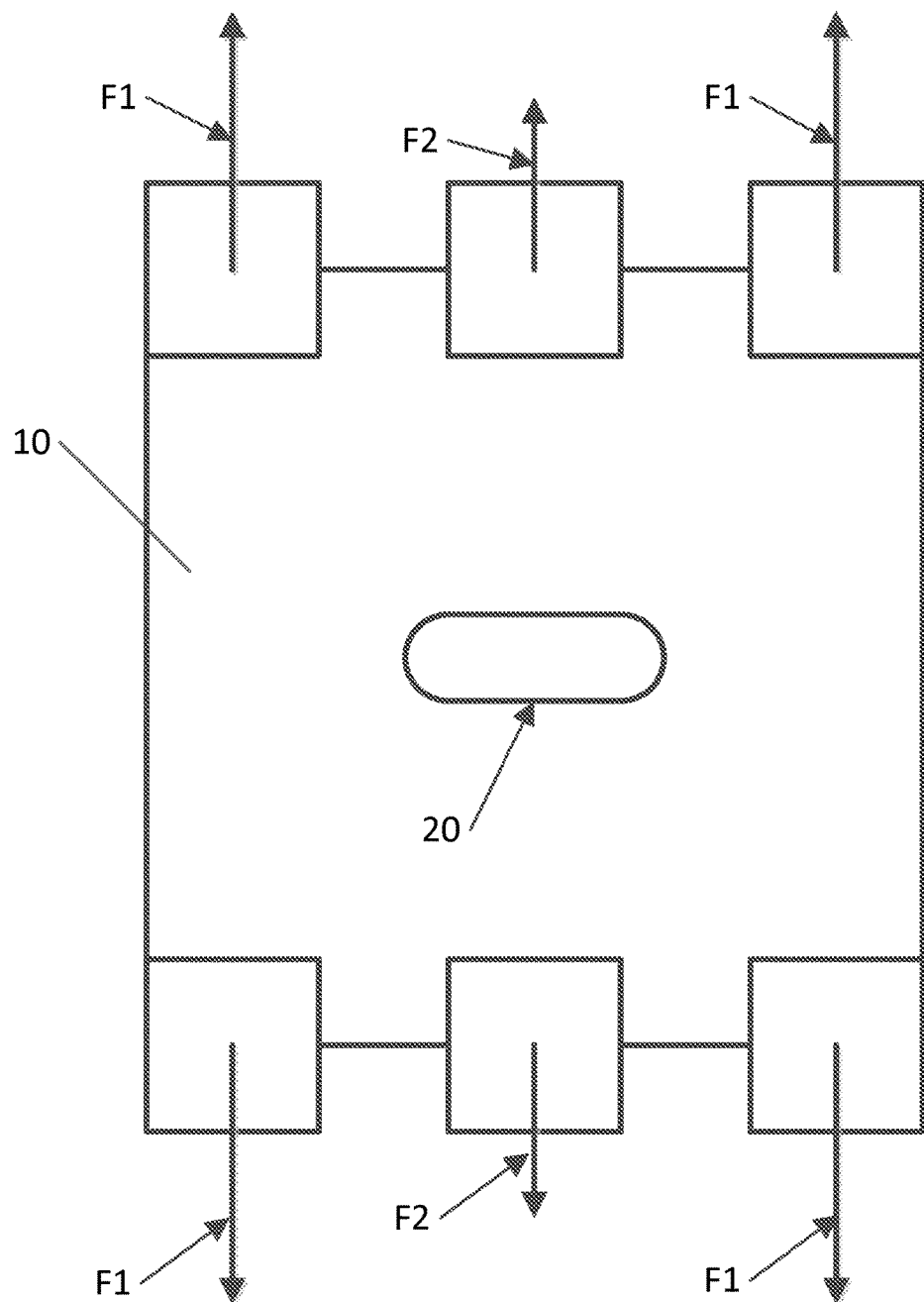
FIG. 1 is a top plan view of an example test coupon.

Referring to FIG. 1, an example test coupon 10 consists of a 2 foot×2 foot panel of laminate composite, or other material, which can be flat or have a non-uniform thickness. Coupon 10 can also have a notch 20 formed in coupon 10, which can be used to simulate or mimic potential damage to a 5 stringer panel, such as those required in some testing of panels for use in aircraft. In the example shown, notch 20 is an elongated slot with rounded end, but can be any shape or size as desired or required for a specific application or test.

Figure 2:
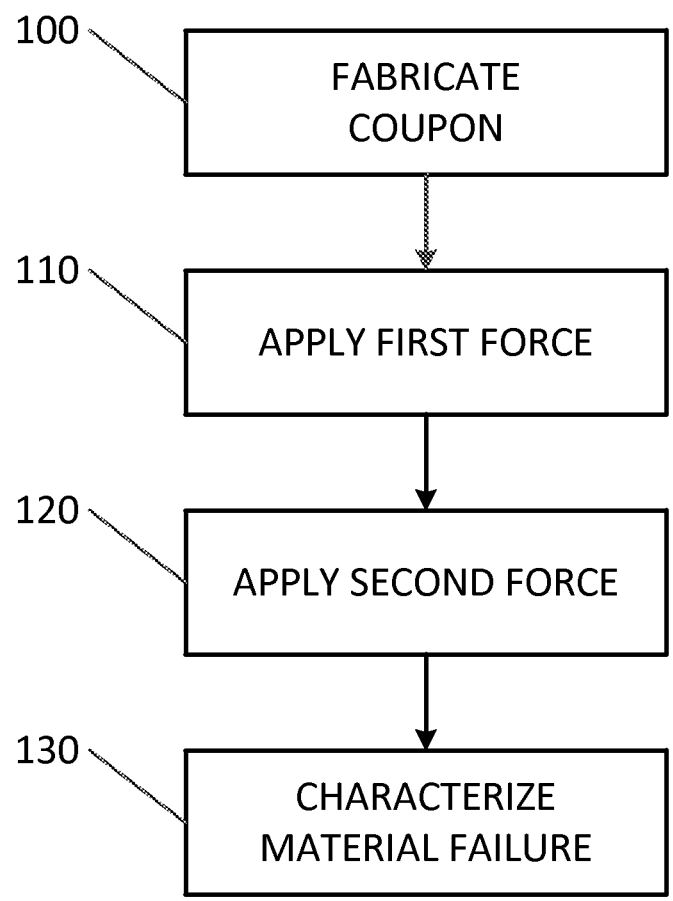
FIG. 2 is a flow diagram of an example method for testing a material coupon.

Referring to FIG. 2, an example material test method is shown using the example coupon 10 described above and shown in FIG. 1. Although the example method is described using coupon 10, the method can be used to test any material of any size, structure, material, dimension, etc. desired.

At Step 100, test coupon 10 is fabricated. As described above, coupon 10 can be a 2 foot×2 foot laminate composite panel having a notch 20 formed in the coupon 10.

At Step 110, a first force F1 (see FIG. 1) is applied to the material using an actuator or other well know apparatus. First force F1 can be a tension or a compression force, depending on the test being performed.

At Step 120, a second force F2 (see FIG. 1) is simultaneously applied to the material using an actuator or other well know apparatus. Second force F2 can also be a tension or a compression force, depending on the test being performed, and is different that first force F1 (e.g., greater or less than first force F1). For example, in some test scenarios, first force F1 can be two to ten times greater than second force F2.

The stress condition on coupon 10 resulting from the two different forces includes tension/compression and shear, similar to the conditions experienced in a 5 stringer panel, and can simulate the same stress state that the skin sees in a 5 stringer panel.

At Step 130, the material failure is characterized once a composite failure, or structural damage to the material, is observed. Characterizing the material failure can include determining a load at material failure initiation, a failure direction, a failure mode (e.g., initiation and growth), best layups for the stress condition, etc. Since coupon 10 does not contain any stringers, arrestment, large scale damage growth, and stringer disband behavior cannot be determined by testing only the coupon 10.

Figure 3:
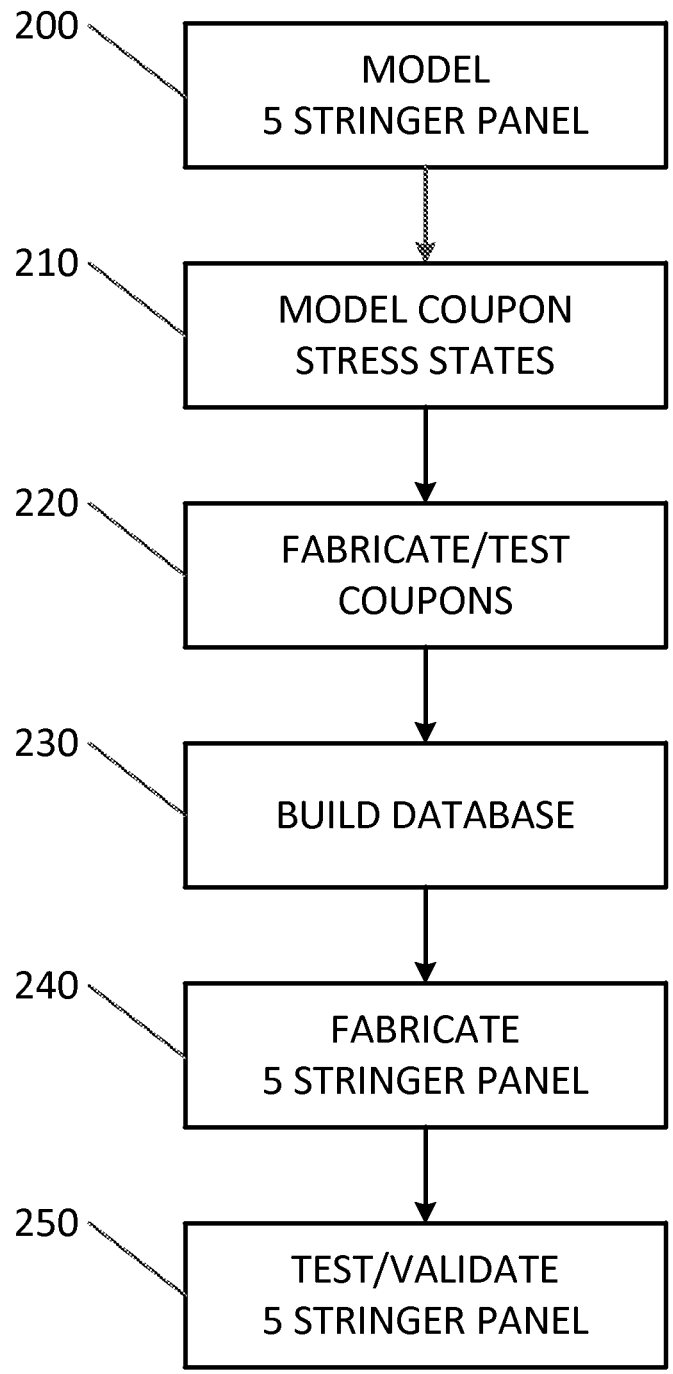
FIG. 3 is a flow diagram of an example method for designing a composite panel.

Referring to FIG. 3, a method of designing a composite panel, such as a 5 stringer panel, using the material test method shown in FIG. 2 is shown.

At Step 200, a composite panel, such as a 5 stringer panel, is modeled using finite element methods (FEM) or other well-known methods and a combined stress state near a notch in the panel is determined.

At Step 210, stress states for a test coupon, such as coupon 10 described above and shown in FIG. 1, are modeled using FEM or other well-known methods to replicate the stress state determined in the modeled 5 stringer panel in Step 200 above. Based on the coupon modeling, values for the first force F1 and the second force F2 are determined.

At Step 220, test coupons 10 are fabricated and tested, as described above in Steps 100-130 and shown in FIG. 2. Due to the lower cost and fabrication time for coupon 10, 20-40 coupons can be fabricated and tested. First force F1 and second force F2 can be varied during testing using sample coupons to match the stress states in the model discussed above.

At Step 230, a database or response surface is built that contains the data gathered in the testing of the coupons 10 in Step 220. The database/response surface can be used by analysis tools and optimizers in the final design of the 5 stringer panel.

At Step 240, a 5 stringer panel is fabricated based on the data contained in the database created in Step 230. Using this method, only one 5 stringer panel has to be fabricated to validate/verify the analysis and certify the design rather than fabricating multiple 5 stringer panels in an attempt to analyze various design and/or optimize a design.

At Step 250, the 5 stringer panel fabricated in Step 240 is tested and validated using well-known testing techniques. Even though the number of 5 stringer panels that need to be fabricated and tested has been reduced, they cannot be eliminated. At least one 5 stringer panel will still have to be fabricated and tested in most industries, such as the aircraft industry, for certification purposes.

The method described above and shown in FIG. 3 can reduce the number of required 5 stringer panel tests required to achieve program success, speed up research and development, reduce research and development costs, reduce certification costs associated with new material technologies, and provide more reliable analysis capabilities by filling the known gaps in current methods, tools, and data, without the need to build several trial and error 5 stringer panels.

While various embodiments have been described above, this disclosure is not intended to be limited thereto. Variations can be made to the disclosed embodiments that are still within the scope of the appended claims.

What is claimed is:

1. A method for determining material failure, comprising the steps of:
    fabricating a coupon made of a laminate composite and comprising a notch;
    applying a pair of opposing first forces on the coupon, the pair of opposing first forces providing one of a tension stress or a compression stress on the coupon;
    applying a pair of opposing second forces on the coupon, the pair of opposing second forces providing one of a tension stress or a compression stress on the coupon, wherein the pair of opposing second forces are greater than or less than the pair of opposing first forces, the first forces are applied in a first direction along a plane of the coupon, and the second forces are applied in a second direction along the plane of the coupon, parallel to the first direction; and characterizing a material failure due to the application of the first forces and the second forces.

2. The method of claim 1, wherein the coupon is a two foot by two foot panel.

3. The method of claim 1, wherein the applying the first forces and the second forces on the coupon provides a shear stress to the coupon.

4. The method of claim 1, wherein the first forces and the second forces provide tension stresses.

5. The method of claim 1, wherein the first forces and the second forces provide compression stresses.

6. The method of claim 1, wherein the first forces provide a tension stress and the second forces provide a compression stress.

7. The method of claim 1, wherein the first forces are two to ten times greater than the second forces.

8. The method of claim 1, wherein characterizing the material failure comprises determining at least one of a load at material failure initiation, a failure direction, and a failure mode.

9. A method for designing a composite panel, comprising the steps of:
    modeling, using finite element methods, the composite panel having a first notch and determining a combined stress state near the first notch;
    modeling, using finite element methods, coupon stress states to replicate the combined stress state of the composite panel;
    fabricating a plurality of coupons, each of the plurality of coupons made of a laminate composite and comprising a second notch;
    testing the plurality of coupons and obtaining a plurality of test results, wherein testing the plurality of coupons comprises the steps of;
        determining a pair of opposing first forces and a pair of opposing second forces for testing, wherein the second forces are greater than or less than the first forces;
        applying the first forces on one of the plurality of coupons in a first direction along a plane of the coupon, the first forces providing one of a tension stress or a compression stress to the coupon;

applying the second forces on the one of the plurality of coupons in a second direction along the plane of the coupon, parallel to the first direction, the second forces providing one of a tension stress or a compression stress to the coupon; and characterizing a material failure due to the application of the first forces and the second forces;

building a database based on the test results;

fabricating the panel based on the plurality of test results in the database; and testing the panel.

10. The method of claim 9, wherein the plurality of coupons are two foot by two foot panels.

11. The method of claim 9, wherein applying the first forces and the second forces on the one of the plurality of coupons provides a shear stress to the one of the plurality of coupons.

12. The method of claim 9, wherein the first forces and the second forces provide tension stresses.

13. The method of claim 9, wherein the first forces and the second forces provide compression stresses.

14. The method of claim 9, wherein characterizing the material failure comprises determining at least one of a load at material failure initiation, a failure direction, and a failure mode.

* * * * *